US009358406B2

(12) United States Patent
Prieels et al.

(10) Patent No.: US 9,358,406 B2
(45) Date of Patent: Jun. 7, 2016

(54) METHOD AND APPARATUS FOR PARTICLE BEAM RANGE VERIFICATION

(75) Inventors: Damien Prieels, Court-Saint-Etienne (BE); Alexandre Debatty, Hevillers (BE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 0 days.

(21) Appl. No.: 14/116,964

(22) PCT Filed: May 11, 2012

(86) PCT No.: PCT/EP2012/058836
§ 371 (c)(1),
(2), (4) Date: Jan. 14, 2014

(87) PCT Pub. No.: WO2012/152938
PCT Pub. Date: Nov. 15, 2012

(65) Prior Publication Data
US 2014/0145088 A1    May 29, 2014

(30) Foreign Application Priority Data
May 11, 2011    (EP) .................................... 11165748

(51) Int. Cl.
*G01J 1/42* (2006.01)
*A61N 5/10* (2006.01)
*G01T 1/29* (2006.01)

(52) U.S. Cl.
CPC ............ *A61N 5/1065* (2013.01); *A61N 5/1048* (2013.01); *G01T 1/2914* (2013.01); *A61N 2005/1052* (2013.01); *A61N 2005/1087* (2013.01)

(58) Field of Classification Search
CPC .......................... A61N 5/1065; G01T 1/2914
USPC ........................................................ 250/393
See application file for complete search history.

(56) References Cited

U.S. PATENT DOCUMENTS

2006/0261277 A1* 11/2006 D'Ambrosio et al. ... 250/363.05
2007/0228305 A1* 10/2007 Keppel et al. .............. 250/505.1
(Continued)

FOREIGN PATENT DOCUMENTS

EP    0779081 A2    6/1997
EP    2116277 A1    11/2009
(Continued)

OTHER PUBLICATIONS

Victor Bom et al., "Real-Time Prompt Gamma Monitoring In Spot-Scanning Proton Therapy Using Imaging Through A Knife-Edge-Shaped Slit." IOP Publishing: Physics In Medicine and Biology, vol. 57, 2012, pp. 297-308.
(Continued)

*Primary Examiner* — David Porta
*Assistant Examiner* — Edwin Gunberg
(74) *Attorney, Agent, or Firm* — Fitch, Even, Tabin & Flannery LLP

(57) ABSTRACT

The invention is related to a method and apparatus for verifying the beam range in a target irradiated with a charged hadron beam, such as a proton beam. The beam range is the location of the Bragg peak in the target, being the location where the largest portion of the dose is delivered. The method utilizes a prompt gamma camera provided with a slit-shaped opening, so as to be able to produced a 1-dimensional profile of the dose distribution along the beam line. The camera is mounted with the slit oriented perpendicularly to the beam line. The method comprises the steps of calculating a position of the camera with respect to a target, for a plurality of beam energies and spots to be irradiated. The method further comprises the steps of verifying the beam range for said plurality of spots, and delivering a value representative of the difference between the estimated beam range and the actual beam range. The apparatus of the invention is provided with a positioning module for positioning the camera.

21 Claims, 8 Drawing Sheets

(56) References Cited

U.S. PATENT DOCUMENTS

2011/0057110 A1 3/2011 Testa et al.
2011/0284757 A1* 11/2011 Butuceanu et al. ........... 250/389

FOREIGN PATENT DOCUMENTS

EP 2140913 A1 1/2010
WO 2010/000857 A1 1/2010

OTHER PUBLICATIONS

Chul-Hee Min et al., "Prompt Gamma Measurements For Locating The Dose Falloff Region In The Proton Therapy." Applied Physics Letters, vol. 89, No. 18, 2006, 3 pages.

Chul-Hee Min et al., "Development Of An Array-Type Prompt Gamma Detection System For The Online Measurement Of The Range Of The Proton Beam In A Patient: A Monte Carlo Feasibility Study." Journal of the Korean Physical Society, vol. 52, No. 3, Mar. 2008, pp. 889-891.

M. Moteabbed et al., "Monte Carlo Patient Study On The Comparison Of Prompt Gamma and PET Imaging For Range Verification In Proton Therapy." IOP Publishing: Physics In Medicine and Biology, vol. 56, 2011, pp. 1063-1082.

J.C. Polf et al., "Measurement And Calculation Of Characteristic Prompt Gamma Ray Spectra Emitted During Proton Irradiation." IOP Publishing: Physics In Medicine and Biology, vol. 54, 2009, pp. N519-N527.

International Search Report And Written Opinion Of The International Searching Authority, PCT/EP2012/058836, dated Nov. 23, 2012, 18 pages.

* cited by examiner

METHOD AND APPARATUS FOR PARTICLE BEAM RANGE VERIFICATION

CROSS REFERENCE TO RELATED APPLICATIONS

This application is a national phase application of International Application No. PCT/EP2012/058836, filed May 11, 2012, designating the United States and claiming priority to European Patent Application No. 11165748.2, filed May 11, 2011, both of which are incorporated by reference as if fully rewritten herein.

FIELD OF THE INVENTION

The invention is related to the field of charged Hadron Therapy, i.e. radiation therapy using particles, such as protons or ions (e.g. carbon ions). More particularly, the invention is related to the measurement of the beam range of a charged hadron beam in a target object.

STATE OF THE ART

It is well established that charged hadrons (i.e., protons, pions, ions such as carbon ions) have physical advantages with respect to X-rays or gamma rays in the field of radiation therapy. For example, protons of a given energy (i.e. forming a mono-energetic proton beam), have a certain penetration depth in a target object and do not penetrate beyond that depth, and furthermore, they deposit their maximum amount of energy or dose in the so-called Bragg Peak, which defines said penetration depth, i.e. the point of greatest penetration of the radiation in the target volume. The position of the Bragg peak is also referred as the 'beam range'. Since the Bragg peak position depends on the energy of the hadron beam, it is evident that by precisely controlling and modifying the energy, one can place the Bragg Peak at a given depth of a tumour so as to administer the greatest radiation energy to selected points and spare the healthy tissue surrounding said points.

As a consequence, the location of the Bragg peak must be precisely controlled since critical tissue localized near the target tumour could receive overdoses, whereas conversely the target tumour could receive underdoses, in case of range error. There is a need therefore to obtain a direct on-line, i.e. during beam delivery, measurement of the particle range.

One option which has been explored is the detection of prompt gammas emitted from a target irradiated by a charged hadron beam. Prompt gammas are emitted isotropically from every location along the charged hadron beam path in the target, so that this path is seen as a gamma line source by a detection apparatus. The detection of said prompt gammas offers a possibility of determining the beam range.

Document WO-A-2010/000857 discloses an apparatus wherein a pin-hole camera is used in conjunction with a scintillator and a 2-dimensional array of photodetectors. Such an apparatus allows to detect the dose fall-off region without requiring a movement of the detectors with respect to the target.

So far no clear methodology or hardware has been developed for the utilisation of such camera systems in a hadron therapy environment.

AIMS OF THE INVENTION

It is an object of the present invention to provide the methodology and hardware for utilising a prompt gamma detection device for the verification of a charged hadron beam range.

SUMMARY OF THE INVENTION

The invention is related to a method and apparatus for verifying the beam range in a target irradiated with a charged hadron beam, such as a proton beam as disclosed in the appended claims. The beam range is the location of the Bragg peak in the target, being the location where the largest portion of the dose is delivered. The method utilizes a prompt gamma camera provided with a slit-shaped opening, so as to be able to produce a 1-dimensional profile of the dose distribution along the beam line. The camera is mounted with the slit oriented perpendicularly to the beam line. The method comprises the steps of calculating a position of the camera with respect to a target, for a plurality of beam energies and spots to be irradiated. The method further comprises the steps of verifying the beam range for said plurality of spots, and delivering a value representative of the difference between the estimated beam range and the actual beam range. The apparatus of the invention is provided with a positioning module for positioning the camera.

The invention is related to a method for verifying the beam range in a target irradiated by a charged hadron beam, in an installation comprising:
  a particle accelerator,
  a nozzle configured to deliver a charged hadron beam along a beam line,
  a target support system for supporting a target in a position with respect to said beam line,
  a prompt gamma camera provided with a slit-shaped opening, the field of view of said camera being significantly wider than the width of the slit-shaped opening,
said method comprising the steps of
  receiving an irradiation plan for a target, comprising the following data or data which allow to define the following data:
    the position of the target relative to the nozzle,
    one or more beam energies of a particle beam to be delivered from the prescribed nozzle position,
    for each energy: the location of one or more spots situated in the target and in a plane that is perpendicular to the beam line, wherein said spots are to be irradiated with a beam having the defined energy,
    optionally: the beam charge for each spot.
  for each spot: receiving as a part of said plan, or calculating: the predicted beam range and preferably also the predicted deposited dose,
  for each beam energy: calculating a position of the camera wherein the slit is orthogonal with respect to the beam line, and wherein the iris line of the slit is placed at a location in the direction of the beam line, said location being in between the extremes of the predicted beam ranges for said energy,
  realising the relative position of the target with respect to the nozzle, as prescribed in said irradiation plan,
  for each energy:
    positioning the camera at the calculated position,
    for each spot in the plane corresponding to said energy:
      irradiating the target with the beam energy provided in the irradiation plan, the beam being directed at the spot, detecting by said camera prompt gamma's emitted from the target and deriving therefrom a dose profile in the direction of the beam line, determining from said profile the measured beam range in said target, comparing said beam range with the predicted beam range.

According to an embodiment, the step of irradiating the target is not included in the method of the invention.

According to an embodiment, the method further comprises the step of indicating whether or not the measured beam range is within a predefined distance from the predicted beam range. Preferably, the iris line of the slit shaped opening is as close as possible to the target.

An embodiment of the method of the invention further comprises the following steps:

for each spot, the predicted deposited dose or a value representative thereof is provided in said plan or calculated, in addition to said step of determining a value of the measured beam range, the deposited dose or a value representative of the deposited dose is determined from said profile, said value is compared to the predicted dose or the value representative thereof.

Preferably, an indication is given whether or not the measured dose is within a predefined range with respect to said predicted dose. Preferably, for each beam energy, the field of view of said camera encompasses the distance between said extremes of the predicted beam ranges for each energy.

An embodiment of the method further comprises the steps of:

estimating the accuracy of the beam range measurement, assessing whether or not the measured beam range falls within an interval defined by said accuracy.

The invention is equally related to an apparatus for verifying the beam range in a target irradiated by a charged hadron beam, in an installation comprising:

a particle accelerator, a nozzle configured to deliver a charged hadron beam along a beam line, a target support system for supporting a target in a position with respect to said beam line, a prompt gamma camera (100) provided with a slit-shaped opening (2), the field of view (101) of said camera being significantly wider than the width of the slit-shaped opening (2), said apparatus comprising:

a precalculation module, configured to receive an irradiation plan, said plan comprising the following data or data which allow to define the following data:

the position of the target relative to the nozzle, a plurality of beam energies of a charged hadron beam to be delivered from the prescribed nozzle position for each energy: the location of a plurality of spots situated in the target and in a plane that is perpendicular to the beam line, wherein said spots are to be irradiated with a beam having the defined energy, optionally: the beam charge for each spot.

for each spot: receive as a part of said plan or calculate the predicted beam range and preferably the predicted dose deposited at the location of the predicted beam range, calculate a position of the camera wherein the slit is orthogonal with respect to the beam line and wherein the iris line of the slit is placed at a location in the direction of the beam line, in between (and including) the extremes of the predicted beam ranges for each of said energy levels a positioning module, configured to position the camera at said position, a verification module, configured to provide an output representative of the difference between the predicted beam range and the beam range as measured by the camera positioned in said position.

In an apparatus according to the invention, said verification module may further be configured to provide a second output representative of the difference between the predicted deposited dose and the dose as measured by the camera positioned in said position.

An apparatus of the invention may further comprise an actuation module, configured to receive a signal representative of said difference or differences, and configured to apply on the basis of said signal, corrective measures to one or more parameters of the irradiation installation, during the irradiation of a target or after irradiation of a target.

According to an embodiment, the apparatus of the invention is suitable for operation with an irradiation installation comprising a rotatable gantry, wherein said positioning module comprises a means for rotating the camera around a rotational axis that coincides with the rotation axis of the gantry, and a means for moving the camera linearly in the direction of said rotation axis of the gantry.

According to another embodiment, said positioning module comprises a robotic arm onto which the camera is mounted, so that the camera can be moved with six degrees of freedom.

According to another embodiment, said positioning module comprises a means for moving the camera with respect to a target, along a trajectory that is fixed with respect to said target.

According to another embodiment, said positioning module comprises an arm extending in a direction parallel to the beam line of a beam produced by the nozzle, said arm, whilst remaining parallel to said beam line, being configured to:

receive the camera attached to an outer end of the arm, be extendable in the direction of the beam line, be rotatable around the beam line, be movable in any radial direction in a plane perpendicular to the beam line.

In the latter embodiment, the apparatus may comprise a plate that is rotatable about the beam line, wherein said arm is slidably arranged in a block which is movable in the radial direction of the plate.

BRIEF DESCRIPTION OF THE FIGURES

FIG. 1a shows a schematic view of an apparatus according to the invention, involving a collimator having a longitudinal slit. FIG. 1b is a section view of the plane A-A' of FIG. 1a. FIG. 1c is a section view of the plane B-B' of FIG. 1a.

DETAILED DESCRIPTION OF THE INVENTION

Figure 1:
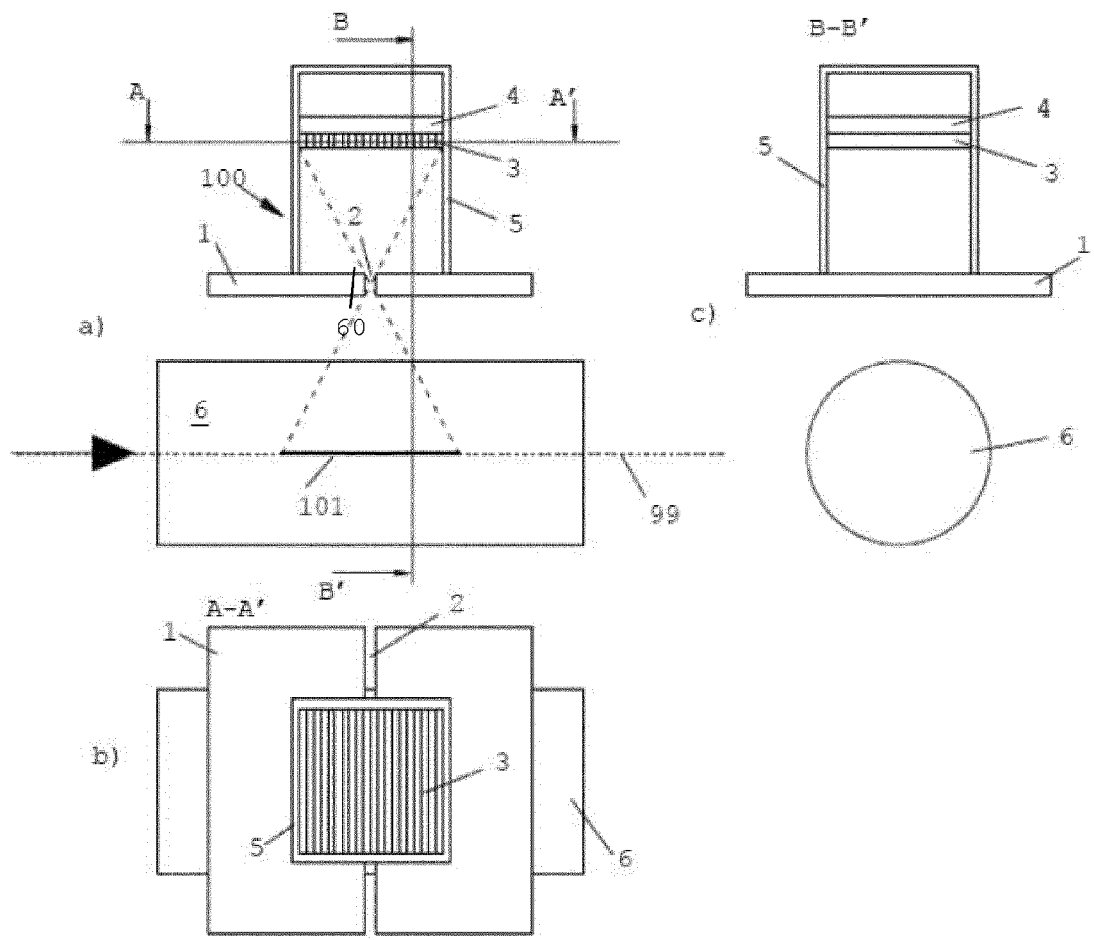

FIG. 1 shows an embodiment of a camera that is applicable in the method of the invention. The camera 100 comprises a collimator 1 with a longitudinal slit-shaped opening 2. In use, the apparatus is mounted next to a target, e.g. a cylindrical water target 6, on which a charged hadron beam, e.g. a proton beam impinges in the direction of the arrow, and follows a path defined by the beam line 99. The slit 2 is oriented perpendicularly to the beam line. At a distance from the collimator, a scintillator 3 is placed, arranged in association with an array 4 of photon counting devices. As known in the art, the scintillator comprises a scintillating crystal material which is capable of interacting with prompt gammas emitted from the target, said interactions generating the emission of photons, which are detected by the devices in array 4. The scintillator has a flat shape parallel to the beam direction, e.g. a rectangular or square shape as shown in the drawing, so that one flat surface of the scintillator faces the longitudinal slit 2 at a predefined distance from said slit.

The thickness of the collimator and the shape of the slit as seen in cross-section taken perpendicularly to the longitudinal axis of the slit, is such that prompt gammas emitted from a zone of the target corresponding to portion 101 of the beam line may enter through the slit 2 and be projected onto the scintillator. Said portion 101 may be referred to as the visible field of view of the camera. The visible field of view is considerably larger than the width of the slit-shaped portion 2, i.e. the camera allows to detect prompt gamma emitted not only from the direction which is at 90° with respect to the beam direction. In other words, the field of view is an area that is significantly wider than the slit-shaped opening that is projected through said opening, onto the detecting means. The visible field of view may be equal to or smaller than the length of the beam line within the target.

The longitudinal form of the slit-shaped portion 2 is advantageous in that it allows a 1-dimensional view of the photon count in the field of view. During data treatment, events are selected belonging to energy windows (for example between 3 MeV and 7 MeV), corresponding to prompt gammas and these events are integrated in bins (of typically 5 mm width) along the beam axis. As a result, a 1D projected image is obtained along the beam axis of the proton beam path inside the target with reasonable statistics and spatial resolution, without moving the detector.

The detected field of view is determined by the width of the scintillator 3 in the direction parallel with the beam. Preferably but not necessarily, the detected field of view is equal to the visible field of view. The scintillator may be divided in segments arranged side by side in said direction parallel to the beam (i.e. the segments themselves are perpendicular to the beam direction), so that prompt gammas are detected in each segment individually, each segment corresponding with a portion of e.g. 5 mm within the field of view. In other words, an 1-dimensional array of scintillator segments is provided. The scintillator may also be formed of a 2-dimensional array of scintillator segments.

The integration in each 5 mm-portion may be done by applying the segmented scintillator of FIG. 1, wherein the events in each segment are integrated to yield a photon count for each 5 mm-wide portion along the beam axis (i.e. a 1-dimensional graph). Alternatively, the scintillator may be uniform instead of segmented, and the integration is done purely on the basis of the output of the photon counting devices (when a 2-D array of photon counting devices is present).

The array 4 of photon counting devices can be an array of photomultiplier tubes or other detector means known in the art, e.g. Silicon drift detectors (SDD) or Silicon avalanche photodiodes (Si APD). The array of photon counting devices is used to determine both the energy deposited in the crystal by the photon interaction and the position/location of this interaction in the scintillator. In the embodiment shown, the array 4 is a two-dimensional array of detectors, placed in a plane parallel to the plane of the scintillator.

Figure 2:
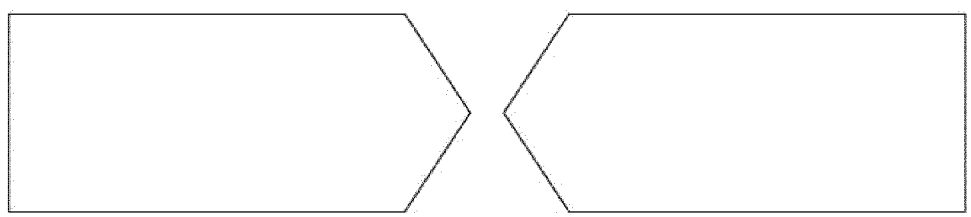
FIG. 2 illustrates an embodiment of a slit with a double conical shape as seen in cross-section.

The projection of the field of view can be obtained for a variety of slit shapes as seen in cross section perpendicular to the longitudinal slit direction. It can be obtained with a slit having parallel side walls as shown in FIG. 1, provided that the collimator thickness is sufficiently low with respect to the width of the slit. According to preferred embodiments, the slit has a conical shape, as illustrated in FIG. 2. Independent of the shape of the slit's cross-section, the iris line 60 (FIG. 1) of the slit is defined as the centre line passing through the middle of the slit, as seen in the direction of the width of the slit and in the direction of the thickness of the camera's collimator 1.

A housing 5 encloses the area between the scintillator 3 and the collimator 1, wherein the housing comprises the detector array and the scintillator and the housing is fixed with respect to the collimator. The housing may be produced from the same material as the collimator. The housing may form a single body with the collimator.

As stated, a selection is preferably made of the energy of the detected particles emitted from the target, within a given energy window. This is done to select unscattered high energy prompt gammas and exclude, as much as possible, neutrons and low energy scattered gammas. According to a preferred embodiment, only prompt gammas with energy between 3 and 7 MeV are selected. A suitable means (as known in the art) needs to be provided in connection with the camera for performing said selection. Suitable calculation and representation means (not shown) are furthermore needed to derive from the detected prompt-gamma a dose-related distribution (preferably the photon count), and to represent said distribution, preferably in the form of a 1-dimensional view, as a function of the position in the field of view 101 in the beam direction, e.g. a graph on a display. From this graph, the position of the Bragg peak can be determined.

The method of the invention utilizes a prompt gamma camera 100 as described above. The method is applied in an installation comprising:
- a particle accelerator, for example comprising a cyclotron, and preferably a number of deflection magnets for guiding a beam along a predefined path towards the nozzle,
- a nozzle configured to deliver a charged hadron beam along a beam line. This may be a moveable nozzle, for example a nozzle attached to a rotatable gantry, the gantry defining an irradiation enclosure in which a target can be positioned. In the preferred field of application, the target is an organ or a tumour in a patient, and the enclosure is a treatment room. The nozzle is preferably provided with sweeping magnets, configured to deflect the beam and perform a beam scan directed to a number of spots located in a zone around the beam line. The beam line is thus defined as the direction of the beam when the sweeping magnets are not activated (or not present).
- a target support system for supporting a target in a position with respect to said beam line. This may be a patient positioning system (PPS) as known in the art.
- a prompt gamma camera 100 provided with a slit-shaped opening 2 as described above, i.e. the field of view (101)

of said camera being significantly wider than the width of the slit-shaped opening (2).

The method comprises the steps of:
receiving an irradiation plan for a target, comprising the following data or data which allow to define the following data:
  the position of the target relative to the nozzle. This may be provided as a predefined position of the target with respect to the isocenter of a rotatable gantry, together with the gantry position with respect to the target,
  one or more beam energies of a particle beam to be delivered from the prescribed nozzle position,
  for each energy: the location of one or more spots situated in the target and in a plane that is perpendicular to the beam line, wherein said spots are to be irradiated with a beam having the defined energy. In the case of a plurality of spots irradiated with the same energy, this is done by deflecting said beam with the sweeping magnets, and sequentially pointing the beam at said spots. Practically, the irradiation plan may comprise actuation voltages for the sweeping magnets, which result in scanning the beam in the direction of said spots. As in prior art irradiation plans, said location of the spots is thus defined by a set of X and Y coordinates at each energy, said coordinates defining the position of each spot in the respective planes perpendicular to the beam line, each plane corresponding to a different beam energy.
  optionally: the beam charge for each spot,
  for each spot: receiving as a part of said plan, or calculating: the predicted beam range based on the beam energy and the materials through which the beam passes (e.g. skin and organ tissue of a patient) and preferably also the predicted deposited dose, based on the beam energy, the beam charge and said materials. This could be regarded as a predicted Z-coordinate of each spot. This information is not included in prior art irradiation plans. In the method of the invention, it is this information that will be used to determine the position of the camera during the beam range verification.
  for each beam energy: calculating a position of the camera wherein the slit is orthogonal with respect to the beam line, i.e. perpendicular to said beam line but placed at a distance from said beam line, and wherein the iris line of the slit is placed at a location in the direction of the beam line, in between (and including) the extremes of the predicted beam ranges for said energy. In the basic case where one spot is irradiated, the camera is placed at said predicted beam range. In the case of a plurality of spots, the exact location of the iris line may be chosen judiciously on the basis of the predicted beam ranges, or it may be determined according to various algorithms. For example the position may simply correspond to the average of the predicted beam ranges, or a more complex statistical algorithm may be applied, resulting in a position that is closest to the majority of predicted beam ranges. For example, beam ranges that are far removed from the majority of beam ranges for a particular energy could be regarded as outlier values, and are therefore not included in the calculation for determining the camera position. The distance between the camera and the beam line in the direction perpendicular to the beam line is preferably as small as possible, i.e. the camera is preferably as close as possible to the target. If possible, the distance between the slit and the target (e.g. a tumour in a patient) is not higher than 15 cm.

Figure 3A:
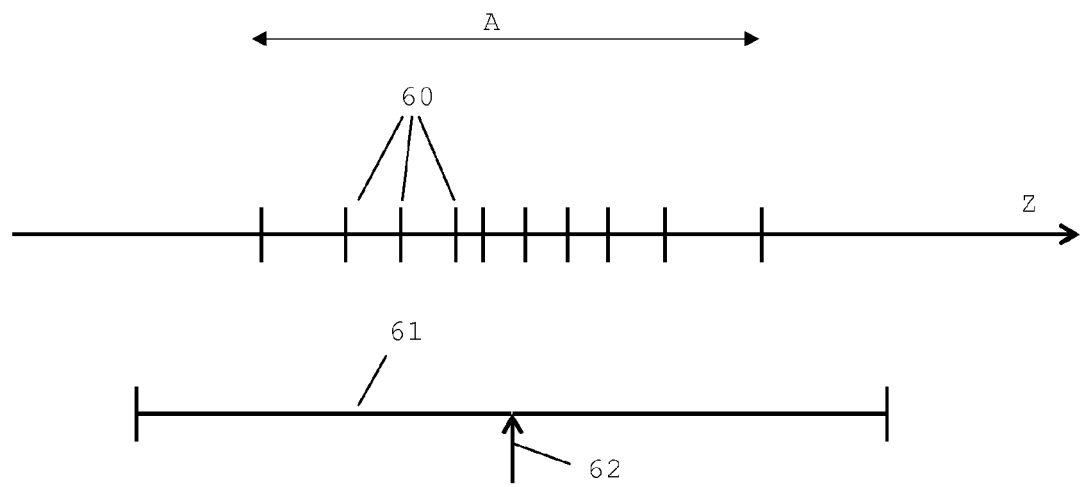
FIG. 3 illustrates the preferred camera position for cameras with various fields of view.

Further with regard to the determination of the camera position, it is preferable that the field of view of the camera is taken into account when determining said position, so that the camera's field of view encompasses all the predicted beam ranges for a given beam energy. This is illustrated in FIG. 3a. The vertical lines 60 represent the predicted beam ranges in a target, arranged along the axis Z. Line 61 represents the field of view of the camera, with the arrow 62 indicating the position of the slit. The camera's position is such that the field of view encompasses the distance A between the two extremes of predicted beam range values (i.e. overlaps and extends on both sides of said distance A).

Figure 3B:
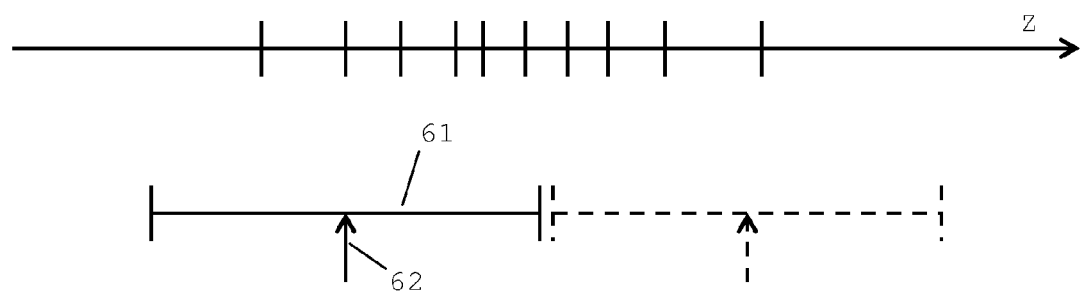

It is possible that the camera's field of view is smaller than the distance between the two extremes of the predicted beam ranges. In that case, the beam range verification cannot be done from one single camera position, and a number of camera positions can be determined for a number of groups of predicted beam ranges. The beam range verification of a particular beam energy is then performed for each of said groups separately. This is illustrated in FIG. 3b, where the dotted line illustrate a second camera position required to verify the beam range for all the spots irradiated at a particular energy.

Regardless of whether the field of view is smaller or larger than the distance A, it is an advantage of the method and apparatus of the invention that a plurality of predicted beam ranges along the Z-axis can be verified from a single camera position.

The foregoing steps represent a pre-calculation phase of the method of the invention. This phase is followed by a measurement phase comprising the following steps:
  realising the relative position of the target with respect to the nozzle, as prescribed in said irradiation plan. This may be done by moving and positioning the target or the nozzle or both,
  for each energy:
    positioning the camera at the determined position,
    for each spot in the plane corresponding to said energy:
      irradiating the target with the beam energy provided in the irradiation plan, the beam being directed at the location of the spot,
      detecting (with said camera) prompt gamma's emitted from the target and deriving therefrom a dose profile in the direction of the beam line,
      determining from said profile a value of the beam range in said target,
      comparing said beam range with the predicted beam range,
      according to a preferred embodiment, the invention further comprises indicating whether or not the measured beam range is within a predefined distance from the predicted beam range.

Given that the method of the invention is a method for verifying a beam range, for example during a proton therapy treatment, and not a method for treatment as such, the step of irradiating the target is not in fact executed by the person putting the method of the invention into practice. The measurement phase may thus be described as:
  realising the relative position of the target with respect to the nozzle, as prescribed in said irradiation plan. This may be done by moving and positioning the target or the nozzle or both,
  for each energy:
    positioning the camera at the determined position,
    for each spot in the plane corresponding to said energy:
      detecting (with said camera) prompt gamma's emitted from the target and deriving therefrom a dose profile in the direction of the beam line,
      determining from said profile a value of the beam range in said target,
      comparing said beam range with the predicted beam range, According to a preferred embodiment, the invention further comprises indicating whether or not the measured beam range is within a predefined distance from the predicted beam range.

The fact that the camera is placed at a predetermined position in between the two extremes of the predicted beam range, and the fact that the camera remains in this position while verifying the beam range at different beam energies is made possible only through the fact that the slit-shaped camera is capable of viewing through a single slit-shaped opening, an area along the beam line that is considerably larger than the width of the slit-shaped opening (see paragraph [0028] hereabove). This feature is not present in existing prompt gamma detection devices equipped with one or more slit-shaped collimator apertures. With regard to the pin-hole prompt gamma camera described in WO-A-2010/000857, the camera that is applied in the method and apparatus of the invention has the advantage that a 1D-view of the dose distribution is obtained, which allows a more accurate and straightforward determination of the beam range.

As already indicated, the above-described method includes the basic embodiment, where a single spot is irradiated by a beam with a prescribed energy. The energy is related to the prescribed beam range, and the camera is positioned at the location corresponding to said predicted range.

The above described method allows to verify whether or not the actual beam range corresponds to the predicted beam range. If the difference is too great, the irradiation may be stopped, or an adjustment can be made to the beam delivery parameters (energy, position of nozzle, etc. . . . ) during the irradiation process, or in a subsequent irradiation of the target (after each spot in the complete target has been irradiated once).

According to an embodiment, the method also comprises the step of determining from the measured profile in each spot a value of the deposited dose at the measured beam range location. This value can be derived from the number of prompt gamma detected by the camera. The method may then further comprise the steps of comparing said measured dose to the predicted dose, possibly followed by stopping the irradiation, or by a corrective action taken during or after the irradiation of the complete target. Instead of providing a value of the predicted dose in the precalculation phase of the method, it is possible also to provide a value of the predicted number of prompt gamma detected by the camera, for instance by making a Monte Carlo simulation that takes into account the atomic structure of the target and the beam charge for that specific spot. It is then possible to directly compare the measured number of prompt gamma with the predicted number. Said comparison is equivalent to the comparison of the predicted and measured dose.

According to an embodiment, the method comprises also the step of calculating the expected accuracy of the beam range measurement, on the basis of the beam energy and the expected dose. The accuracy can be quantified on the basis of a simulation of the beam and target. This provides another criterion by which the irradiation can be assessed. If the beam range is outside the expected accuracy, the irradiation may be stopped, or corrective measures may be applied during or after the irradiation of the target.

The invention is also related to an apparatus arranged in cooperation with an irradiation installation comprising:
 a particle accelerator,
 a nozzle configured to deliver a charged hadron beam along a beam line (as defined above),
 a target support system for supporting a target in a position with respect to said beam line,
 a prompt gamma camera 100 provided with a slit-shaped opening 2, the field of view 101 of said camera being significantly wider than the width of the slit-shaped opening 2.

Figure 4:
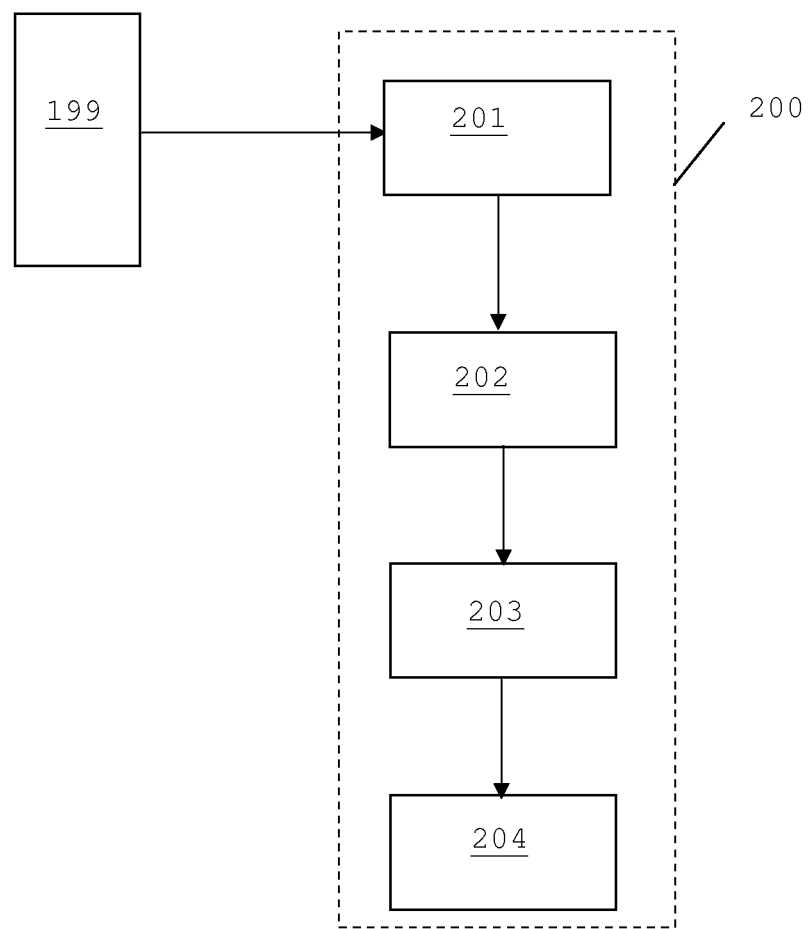
FIG. 4 shows a schematic view of an apparatus for beam range verification according to the invention.

The apparatus 200 of the invention comprises (see schematic outline in FIG. 4):
 a precalculation module 201, configured to
  receive an irradiation plan 199, said plan comprising the following data or data which allow to define the following data:
   the position of the target relative to the nozzle,
   a plurality of beam energies of a particle beam delivered from the prescribed nozzle position,
   for each energy: the location of a plurality of spots situated in the target and in a plane that is perpendicular to the beam line, wherein said spots are to be irradiated with a beam having the defined energy, e.g. by deflecting said beam with the sweeping magnets, and sequentially pointing the beam at said spots,
   optionally: the beam charge for each spot.
  for each spot: receive as a part of said plan or calculate the predicted beam range and preferably the predicted dose deposited at the location of the predicted beam range,
  calculate a position of the camera wherein the slit is orthogonal with respect to the beam line and wherein the iris line of the slit is placed at a location in the direction of the beam line, in between (and including) the extremes of the predicted beam ranges for each of said energy levels,
 a positioning module 202, configured to position the camera at said position,
 a verification module 203, configured to provide an output representative of the difference between the predicted beam range and the beam range as measured by the camera positioned in said position. According to an embodiment, a second output is provided representative of the difference between the predicted dose and the measured dose.

The precalculation and verification modules are basically computers with the capacity for making the above described calculations and comparisons, and providing a readable output. The reduction to practice of these components is therefore not described in detail here as it is considered to be within the competence of a person skilled in the art.

The apparatus may further be provided with an actuation module 204, configured to receive a signal representative of said difference or differences, and configured to apply on the basis of said signal, corrective measures to one or more parameters of the irradiation installation, during the irradiation of a target or after irradiation of a target. Said corrective measures also comprise stopping the operation of an irradiation installation.

Figure 5A:
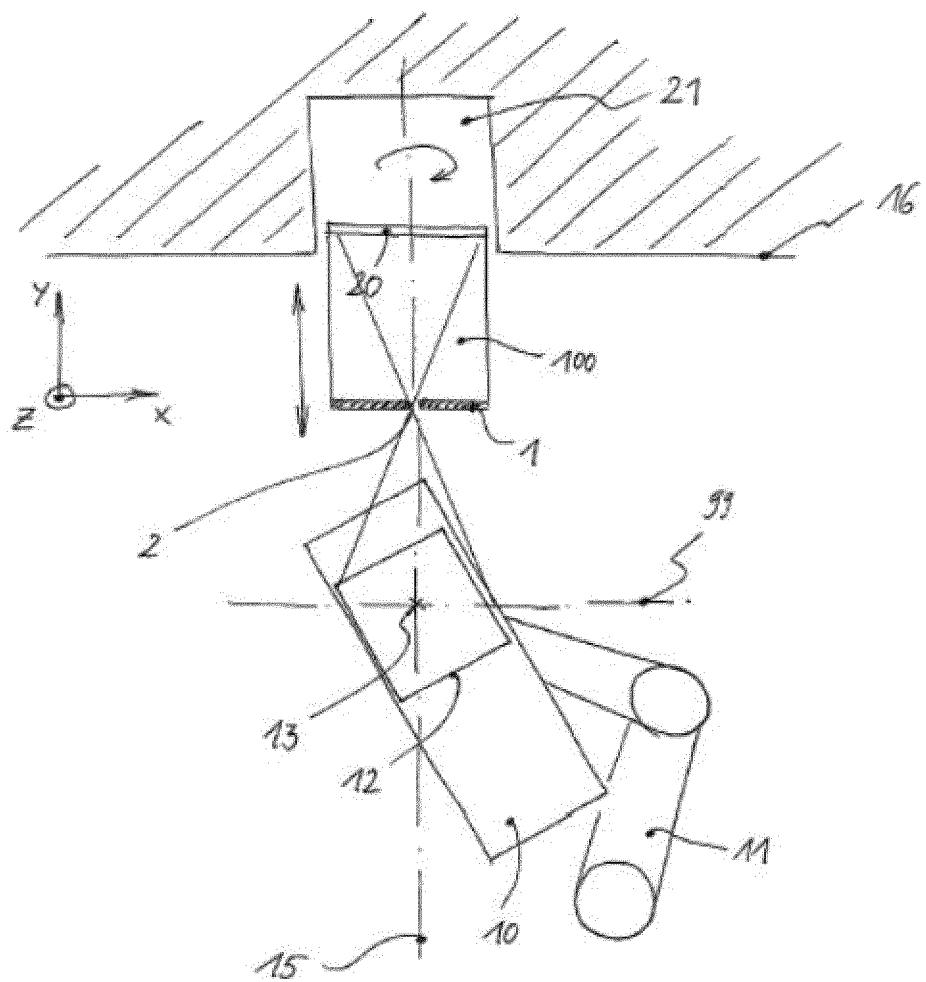
FIG. 5 shows a positioning module according to a first embodiment.
Figure 5B:
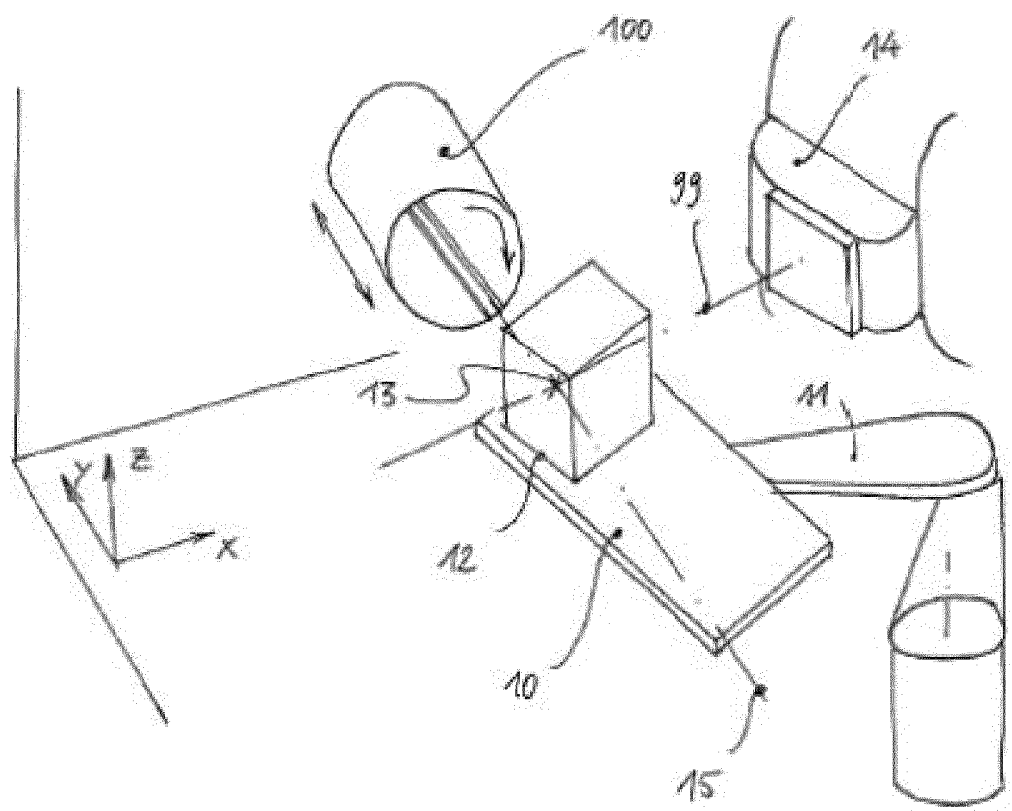

A number of embodiments of the positioning module according to the invention are described hereafter. A first embodiment is shown in FIG. 5a (top view) and FIG. 5b (3D view). The apparatus is shown in the case where the target is positioned on a couch 10, suitable for receiving a patient but the apparatus of the invention is applicable to any type of target. The couch is movable by a patient positioning system (PPS) 11, known as such in the art. The target is represented as a cube 12 with its centre coinciding with the isocenter 13 of a gantry installation. The gantry supports a nozzle 14 which can rotate around the target along a circular path about the horizontal gantry rotation axis 15, so that the nozzle produces a beam through the isocenter 13 from every position. By adjusting the PPS 11 and the nozzle position, any relative position of the nozzle 14 with respect to the target 12 can be realised. The prompt gamma camera 100 is provided in a front wall 16 of the treatment room defined by the rotating gantry. The collimator 1 of the camera is provided with a slit-shaped opening 2 and a detector means 20 (scintillator, detector array) as described above. The camera 100 preferably has a cylindrical outer shape. The camera is stored in a storage location 21, in a position wherein the camera's central axis coincides with the rotation axis 15 of the gantry. The camera is movable with respect to the storage position by rotating it around its central axis (i.e. around the gantry's rotation axis 15), and by a linear movement in and out of the storage location, in the direction of the gantry rotation axis. In this way, by rotating the camera, the position of the slit 2 with respect to the beam line direction 99 can be adjusted so that the slit is orthogonal to said beam line direction. The linear movement allows to position the camera at an optimal position with respect to the target, preferably as close as possible to the target, taking into account possible obstructions. The distance between the camera 100 and the target 12 is preferably measured between the iris line (see definition above) of the camera and the isocenter 13. According to a preferred embodiment, the apparatus further comprises a collision avoidance system (not shown), which preferably comprises one or more sensors configured to sense the distance between the camera and any objects or persons present in the irradiation room, and a system configured to stop the camera when said distance is too small.

Figure 6:
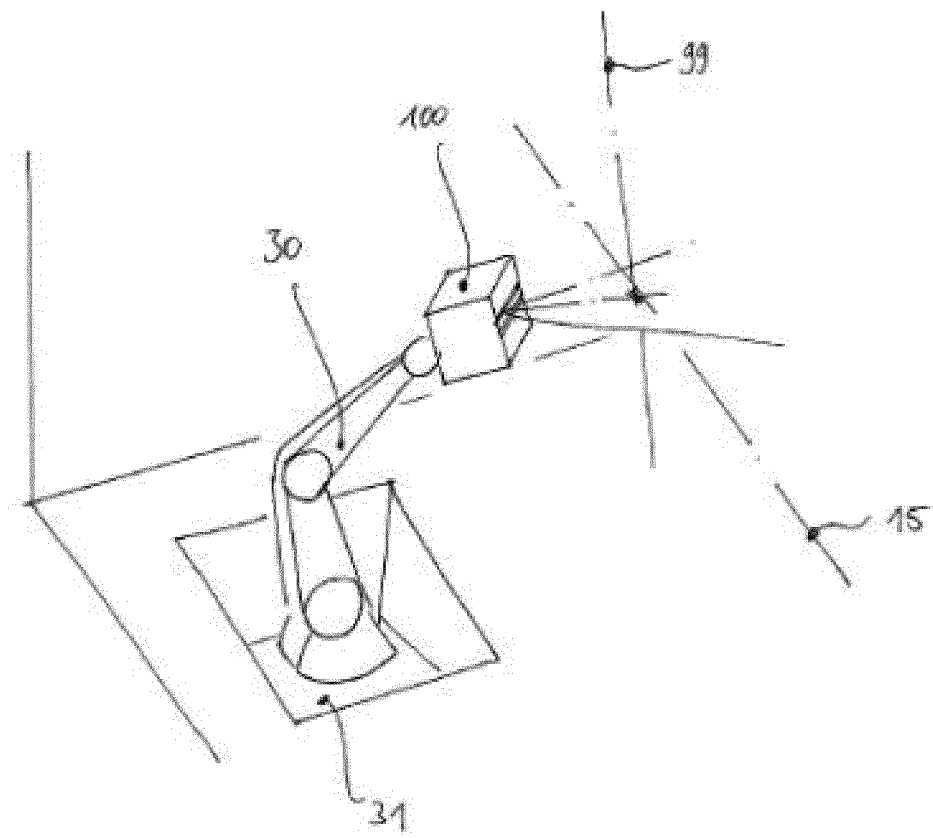
FIG. 6 shows a positioning module according to a second embodiment.

According to a second embodiment, shown in FIG. 6, the camera 100 is mounted on a robotic arm 30 with six degrees of freedom. Such a robot is known as such in the art. The robot may be mounted in conjunction with a gantry and nozzle as described for the previous embodiment. For the sake of simplicity, the drawing only shows the gantry rotation axis 15 and the direction of the beam line 99 from a possible nozzle position. The robot 30 is mounted in a pit or on a pedestal 31 which can be placed in a fixed position with respect to the gantry, so that the robotic arm is free to take up any position relative to a target and a beam line, as soon as the relative position of the nozzle and the target is realised. In this case also, a collision avoidance system is recommended.

Figure 7:
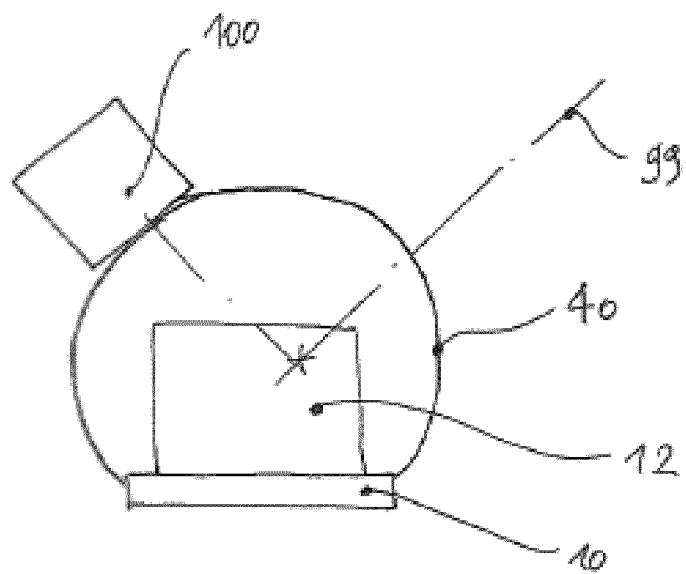
FIG. 7 shows a positioning module according to a third embodiment.

According to a third embodiment, illustrated in FIG. 7, the camera 100 is mounted on a camera guidance rail 40 which is itself mounted on the couch 10. The camera is movably attached to the rail 40. The rail is configured to position the camera at a location around the target. This allows to place the camera at the desired position with respect to the beam line 99.

Figure 8A:
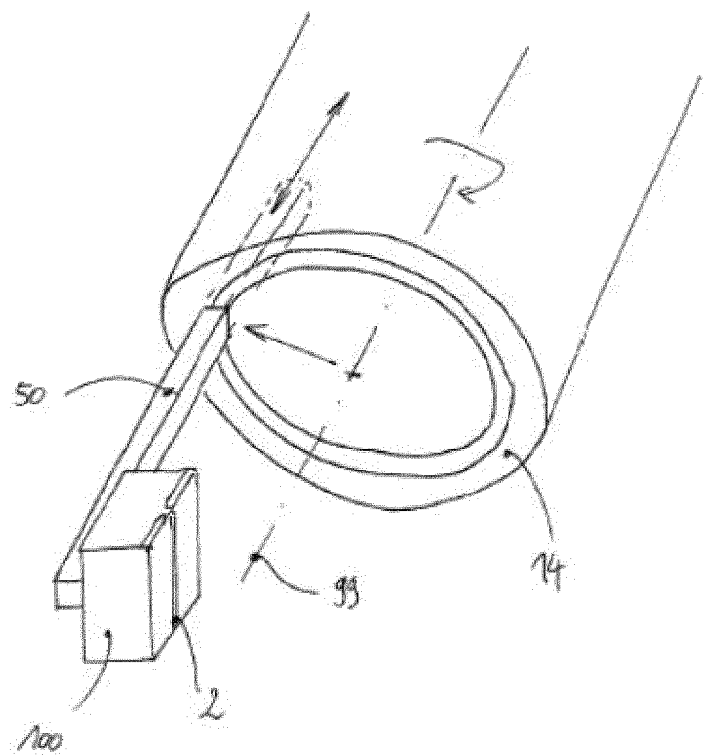
FIG. 8 shows a positioning module according to a fourth embodiment.
Figure 8B:
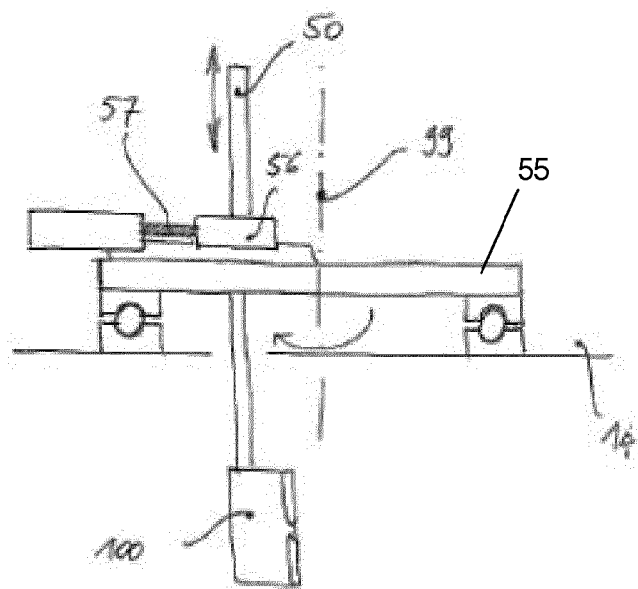
Figure 8C:
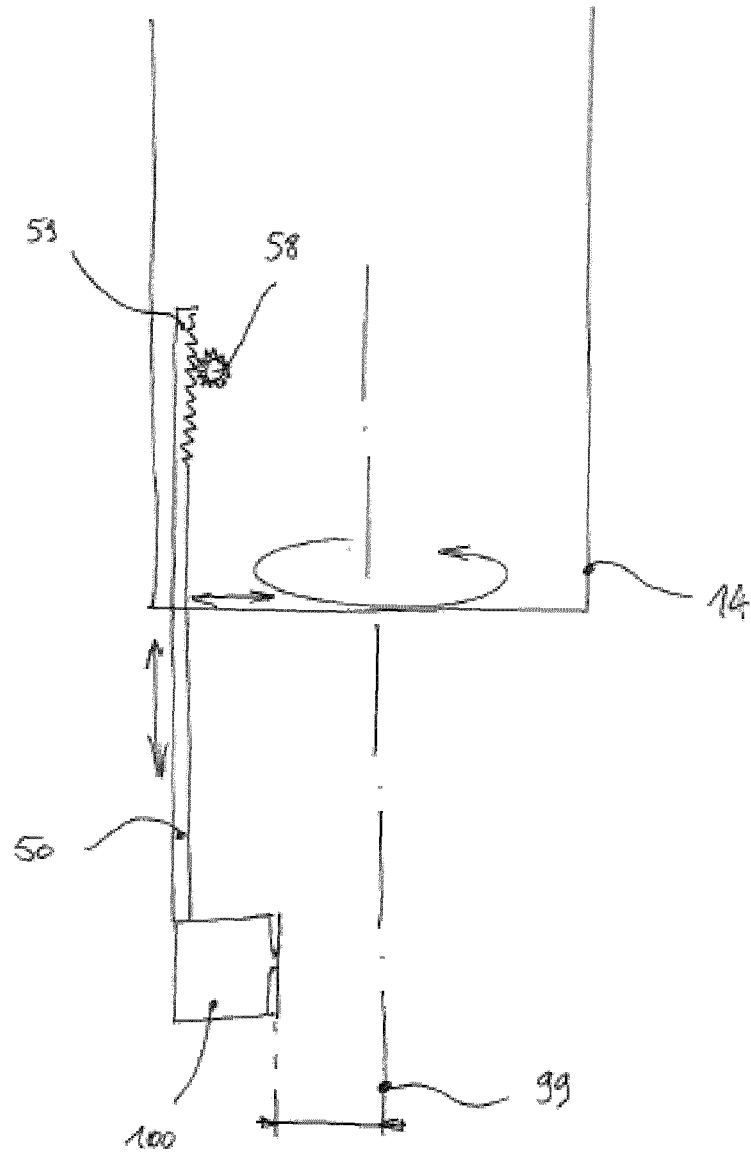

A fourth embodiment is shown in FIGS. 8a/8b/8c. In this case, the camera 100 is attached to an arm 50, which is mounted on the nozzle 14 itself. Whilst remaining parallel to the beam line direction, the arm 50 is rotatable around said beam line, defined by the central axis of the nozzle 14. The camera is mounted at the end of the arm 50, with the slit oriented perpendicularly to the beam line 99. The arm is movable in the direction of the beam line, and in any direction perpendicular to the beam line. In this way, the camera can be positioned at any location with respect to the target, while the slit 2 remains perpendicular to the beam line direction. FIGS. 8b/8c show a possible mechanical apparatus for driving the movement of the arm. A plate 55 is arranged to be rotatable with respect to the nozzle 14, the rotation taking place around the beam line 99 of a beam produced by the nozzle. The plate 55 must have an opening in the middle for the passage of the beam. The arm 50 is slidably arranged in a block 56 which is movable in the radial direction of the plate, e.g. by rotation of a screw 57 oriented in said radial direction and engaging with the block 56. A rotatable gear wheel 58 is configured to engage with gear teeth 59 on the arm 50, for driving the linear movement of the arm in a direction parallel to the beam line 99.

While the invention has been illustrated and described in detail in the drawings and foregoing description, such illustration and description are to be considered illustrative or exemplary and not restrictive. Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The foregoing description details certain embodiments of the invention. It will be appreciated, however, that no matter how detailed the foregoing appears in text, the invention may be practiced in many ways, and is therefore not limited to the embodiments disclosed. It should be noted that the use of particular terminology when describing certain features or aspects of the invention should not be taken to imply that the terminology is being re-defined herein to be restricted to include any specific characteristics of the features or aspects of the invention with which that terminology is associated.

The invention claimed is:

1. An apparatus for verifying the beam range in a target irradiated by a charged hadron beam, in an installation comprising:
   a particle accelerator,
   a nozzle configured to deliver a charged hadron beam along a beam line,
   a target support system for supporting a target in a position with respect to said beam line,
   a prompt gamma camera provided with a slit-shaped opening, the field of view of said camera being significantly wider than the width of the slit-shaped opening, so that the slit shaped opening enables the detection of prompt gamma emitted not only from the direction which is at 90° with respect to the beam line,
said apparatus comprising:
   a precalculation module, configured to:
     receive an irradiation plan comprising the following data or data which allows defining the following data:
       a position of the target relative to the nozzle,
       one or more beam energies of a charged hadron beam to be delivered from a prescribed nozzle position,
       for each energy: the location of one or more spots situated in the target and in a plane that is perpendicular to the beam line, wherein said spots are configured to be irradiated with a beam having a defined energy,
     for each spot: receive as a part of said plan or calculate a predicted beam range,
     calculate a position of the camera wherein the slit-shaped opening is orthogonal with respect to the beam line and wherein an iris line of the slit-shaped opening is placed at a location in the direction of the beam line, in between (and including) the extremes of predicted beam ranges for each of said energy levels,
   a positioning module configured to position the camera at said calculated camera position, a verification module configured to provide an output representative of the difference between the predicted beam range and the beam range as measured by the camera positioned in said calculated camera position.

2. The apparatus according to claim 1, wherein the precalculation module is further configured to receive as part of said plan or calculate for each spot a predicted dose deposited at the location of the predicted beam range, and wherein said verification module is further configured to provide a second output representative of the difference between the predicted deposited dose and the dose as measured by the camera positioned in said calculated camera position.

3. The apparatus according to claim 2, further comprising an actuation module configured to receive a signal representative of said difference, and configured to apply on the basis of said signal, corrective measures to one or more parameters of the irradiation installation, during the irradiation of a target or after irradiation of a target.

4. The apparatus according to claim 1, suitable for operation with an irradiation installation comprising a rotatable gantry, wherein said positioning module is configured to rotate the camera around a rotational axis that coincides with a rotation axis of the gantry, and to move the camera linearly in the direction of said rotation axis of the gantry.

5. The apparatus according to claim 1, wherein said positioning module comprises a robotic arm onto which the camera is mounted, so that the camera can be moved with six degrees of freedom.

6. The apparatus according to claim 1, wherein said positioning module is configured to move the camera with respect to a target, along a trajectory that is fixed with respect to said target.

7. The apparatus according to claim 1, wherein said positioning module comprises an arm extending in a direction parallel to the beam line of a beam produced by the nozzle, said arm, whilst remaining parallel to said beam line, being configured to:
  receive the camera attached to an outer end of the arm,
  be extendable in the direction of the beam line,
  be rotatable around the beam line,
  be movable in any radial direction in a plane perpendicular to the beam line.

8. The apparatus according to claim 7, comprising a plate that is rotatable about the beam line, wherein said arm is slidably arranged in a block which is movable in the radial direction of the plate.

9. The apparatus of claim 1, wherein the irradiation plan further comprises the beam charge for the plurality of spots.

10. A method for verifying the beam range in a target irradiated by a charged hadron beam, in an installation comprising:
  a particle accelerator,
  a nozzle configured to deliver a charged hadron beam along a beam line,
  a target support system for supporting a target in a position with respect to said beam line,
  a prompt gamma camera provided with a slit-shaped opening, the field of view of said camera being significantly wider than the width of the slit-shaped opening, so that the slit shaped opening enables the detection of prompt gamma emitted not only from the direction which is at 90° with respect to the beam line,
  said method comprising the steps of
  receiving an irradiation plan for the target, comprising the following data or data which allows defining the following data:
    a position of the target relative to the nozzle,
    one or more beam energies of a particle beam to be delivered from a prescribed nozzle position,
    for each of said one or more beam energies: the location of one or more spots situated in the target and in a plane that is perpendicular to the beam line, wherein said spots are configured to be irradiated with a beam having a defined energy,
  for each spot: receiving as a part of said plan, or calculating a predicted beam range
  for each of said one or more beam energies: calculating a position of the camera wherein the slit-shaped opening is orthogonal with respect to the beam line, and wherein an iris line of the slit-shaped opening is placed at a location in the direction of the beam line, said location being in between the extremes of the predicted beam ranges for said energy,
  realising a relative position of the target with respect to the nozzle, as prescribed in said irradiation plan,
  for each of said one or more beam energies:
    positioning the camera at the calculated camera position,
    for each spot in the plane corresponding to the beam energy:
      irradiating the target with the beam energy provided in the irradiation plan, the beam being directed at the spot,
      detecting by said camera prompt gammas emitted from the target and deriving therefrom a dose profile in the direction of the beam line,
      determining from said dose profile the measured beam range in said target,
      comparing said beam range with the predicted beam range.

11. The method according to claim 10, further comprising the step of indicating whether or not the measured beam range is within a predefined distance from the predicted beam range.

12. The method according to claim 10, wherein said position of the camera is further defined by the iris line of the slit shaped opening being as close as possible to the target.

13. The method according to claim 10, further comprising:
  for the one or more spots, receiving or calculating the predicted deposited dose or a value representative thereof,
  in addition to said step of determining a value of the measured beam range, determining the deposited dose or a value representative of the deposited dose from said profile,
  and comparing said value to the predicted dose or the value representative thereof.

14. The method according to claim 13, wherein an indication is given whether or not the measured dose is within a predefined range with respect to said predicted dose.

15. The method according to claim 10, further comprising the steps of:
  estimating the accuracy of the beam range measurement,
  assessing whether or not the measured beam range falls within an interval defined by said accuracy.

16. The method according to claim 10, wherein for the one or more beam energies, the position of the camera is such that the field of view of said camera encompasses the distance between said extremes of the predicted beam ranges for said energy.

17. The method according to claim 10, wherein the irradiation plan further comprises the beam charge for the plurality of spots.

18. An apparatus for measuring the beam range in a target irradiated by a charged hadron beam, in an installation comprising:
  a particle accelerator,
  a nozzle configured to deliver a charged hadron beam along a beam line, a target support system for supporting a target in a position with respect to said beam line, a prompt gamma camera provided with a slit-shaped opening, the field of view of said camera being significantly wider than the width of the slit-shaped opening, so that the slit shaped opening enables the detection of prompt gamma emitted not only from the direction which is at 90° with respect to the beam line, said apparatus comprising:
i) a precalculation module, configured to
   A) receive an irradiation plan comprising the following data or data which allows defining the following data:
      a) a position of the target relative to the nozzle,
      b) one or more beam energies of a charged hadron beam to be delivered from a prescribed nozzle position,
      c) for each energy: the location of one or more spots situated in the target and in a plane that is perpendicular to the beam line, wherein said spots are configured to be irradiated with a beam having a defined energy,
   B) for each energy level:
      a) receive as a part of said plan or calculate a predicted beam range for at least one of the one or more spots,
      b) calculate a position of the camera wherein the slit-shaped opening is orthogonal with respect to the beam line and wherein an iris line of the slit-shaped opening is placed at a location in the direction of the beam line, in between (and including) the extremes of predicted beam ranges,
ii) a positioning module, configured to position the camera at said calculated camera position.

19. Apparatus according to claim 18, further comprising a verification module, configured to provide an output representative of the difference between the predicted beam range and the beam range as measured by the camera positioned in said calculated camera position.

20. A method for measuring the beam range in a target irradiated by a charged hadron beam, in an installation comprising: a particle accelerator,
   a nozzle configured to deliver a charged hadron beam along a beam line,
   a target support system for supporting a target in a position with respect to said beam line,
   a prompt gamma camera provided with a slit-shaped opening, the field of view of said camera being significantly wider than the width of the slit-shaped opening, so that the slit shaped opening enables the detection of prompt gamma emitted not only from the direction which is at 90° with respect to the beam line, said method comprising the steps of
   i) receiving an irradiation plan for the target, comprising the following data or data which allows defining the following data:
      A) the position of the target relative to the nozzle,
      B) one or more beam energies of a particle beam to be delivered from a prescribed nozzle position,
      C) for each of said one or more beam energies: the location of one or more spots situated in the target and in a plane that is perpendicular to the beam line, wherein said spots are configured to be irradiated with a beam having a defined energy,
   ii) realising a relative position of the target with respect to the nozzle, as prescribed in said irradiation plan,
   iii) for each of said one or more beam energies:
      a) receiving as a part of said plan, or calculating a predicted beam range for at least one of the one or more spots,
      b) calculating a position of the camera wherein the slit-shaped opening is orthogonal with respect to the beam line, and wherein an iris line of the slit-shaped opening is placed at a location in the direction of the beam line, said location being in between the extremes of the predicted beam ranges,
      c) positioning the camera at the calculated camera position,
      d) for one or more spots: irradiating the target with the beam energy provided in the irradiation plan, the beam being directed at the spot, detecting by said camera prompt gammas emitted from the target and deriving therefrom a dose profile in the direction of the beam line, determining from said dose profile the measured beam range in said target.

21. Method according to claim 20, further comprising the step of comparing said beam range with the predicted beam range.

* * * * *